(12) United States Patent
Lem et al.

(10) Patent No.: US 10,495,669 B2
(45) Date of Patent: Dec. 3, 2019

(54) SENSOR FOR CONTACTLESS ELECTROCARDIOGRAPHIC MEASUREMENT

(71) Applicant: FORD GLOBAL TECHNOLOGIES, LLC, Dearborn, MI (US)

(72) Inventors: Jeroen Lem, Maastricht (NL); Benjamin Eilebrecht, Herne NRW (DE); Marcel Mathissen, Wuerselen NRW (DE); Achim Lindner, Euskirchen (DE); Rainer Vogt, Aachen NRW (DE); Marian Walter, Aachen (DE); Steffen Leonhardt, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 487 days.

(21) Appl. No.: 14/466,410

(22) Filed: Aug. 22, 2014

(65) Prior Publication Data

US 2015/0054495 A1      Feb. 26, 2015

(30) Foreign Application Priority Data

Aug. 22, 2013  (DE) .................. 10 2013 216 682

(51) Int. Cl.
*G01R 1/067*          (2006.01)
*A61B 5/0408*         (2006.01)
(Continued)

(52) U.S. Cl.
CPC ........ *G01R 1/06794* (2013.01); *A61B 5/0408* (2013.01); *A61B 5/6891* (2013.01); *F04B 45/027* (2013.01); *G01L 1/00* (2013.01)

(58) Field of Classification Search
None
See application file for complete search history.

(56) References Cited

U.S. PATENT DOCUMENTS 5,815,864 A * 10/1998 Sloop ................. A61G 7/05769
                                                      5/706
6,158,768 A * 12/2000 Steffens, Jr. ...... B60R 21/01532
                                                      180/237
(Continued)

FOREIGN PATENT DOCUMENTS

DE    102008049112 A1    5/2009
DE    202012001096 U1    3/2012
(Continued)

OTHER PUBLICATIONS

Machine English Translation of JP 2009172204A.*
German Patent Office, Search Report for the corresponding German Patent Application No. 10 2013 216 684.2 dated Mar. 11, 2014.

*Primary Examiner* — Douglas X Rodriguez
(74) *Attorney, Agent, or Firm* — Brooks Kushman PC; David Kelley

(57) ABSTRACT

A sensor for a contactless electrocardiographic measurement on a person includes a carrier for fastening the sensor on an object, such as a vehicle seat, and at least one electrically flat electrode mounted to the carrier by an elastic element. An inflatable bellows is disposed between the carrier and the electrode, inflation of the bellows deflecting the elastic element and increasing a distance between the electrode and the carrier to thereby urge the electrode toward a person seated on the seat.

3 Claims, 4 Drawing Sheets

(51) Int. Cl.
  *A61B 5/00* (2006.01)
  *F04B 45/027* (2006.01)
  *G01L 1/00* (2006.01)

(56) References Cited

U.S. PATENT DOCUMENTS

| | | | |
|---|---|---|---|
| 6,968,263 B1 * | 11/2005 | Norton | B60R 21/01532 |
| | | | 280/728.1 |
| 7,315,754 B2 | 1/2008 | Leonhardt et al. | |
| 8,886,334 B2 * | 11/2014 | Ghaffari | A61B 1/00082 |
| | | | 607/115 |
| 9,014,824 B2 | 4/2015 | Kroll-Orywahl et al. | |
| 2012/0259181 A1 * | 10/2012 | Fujita | A61B 5/18 |
| | | | 600/300 |
| 2014/0039595 A1 * | 2/2014 | Kroll-Orywahl | A61F 5/028 |
| | | | 607/149 |
| 2014/0334653 A1 * | 11/2014 | Luna | G05B 15/02 |
| | | | 381/332 |

FOREIGN PATENT DOCUMENTS

| | | |
|---|---|---|
| EP | 2532306 A1 | 12/2012 |
| JP | 2009172204 A * | 8/2009 |

\* cited by examiner

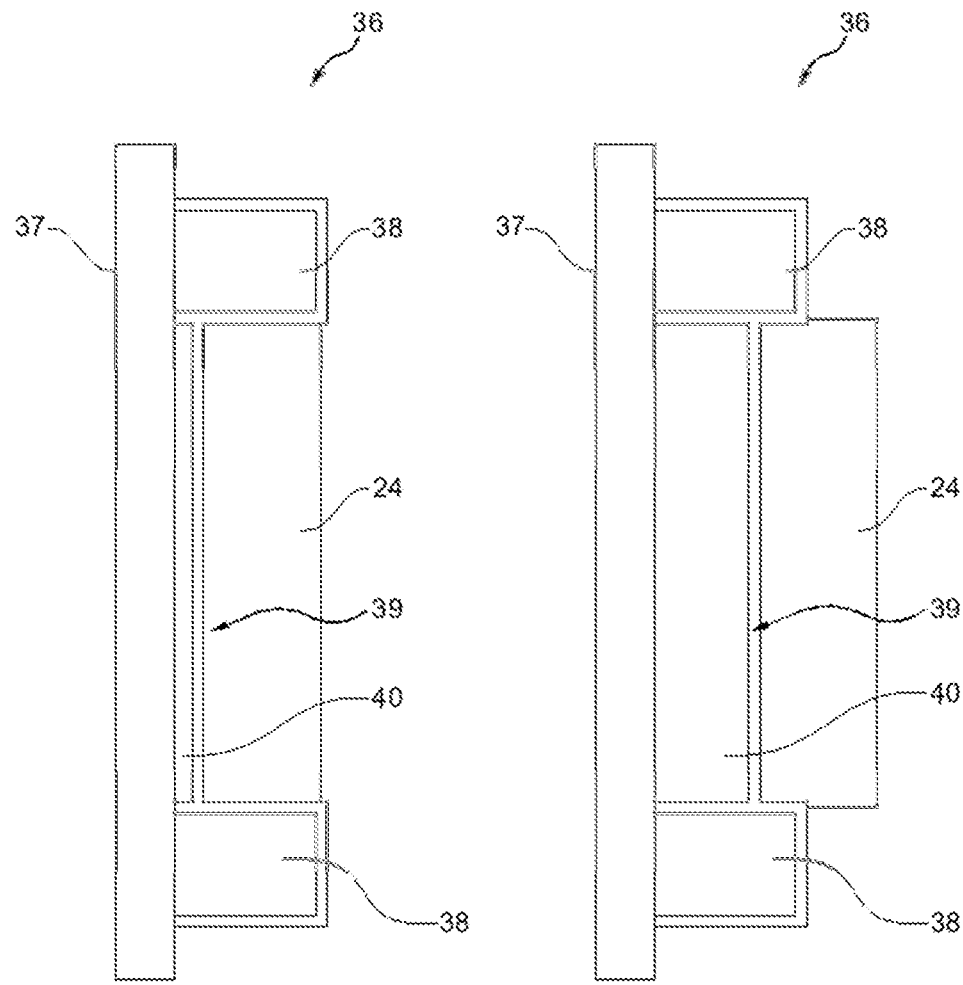

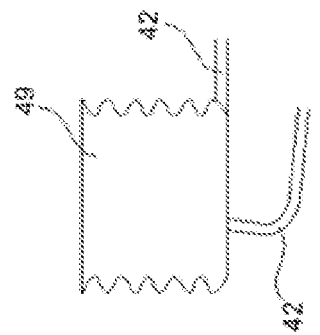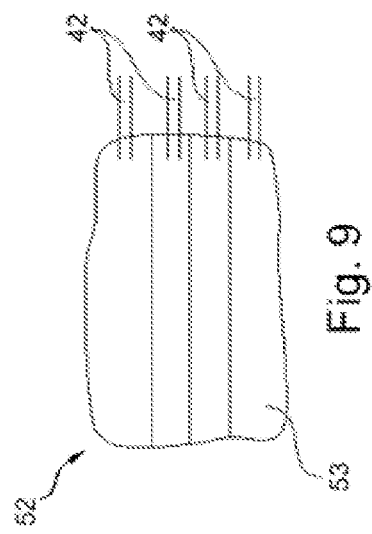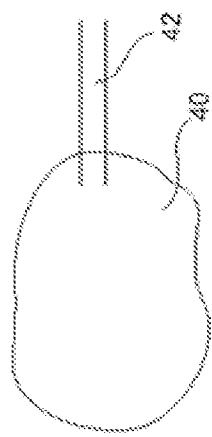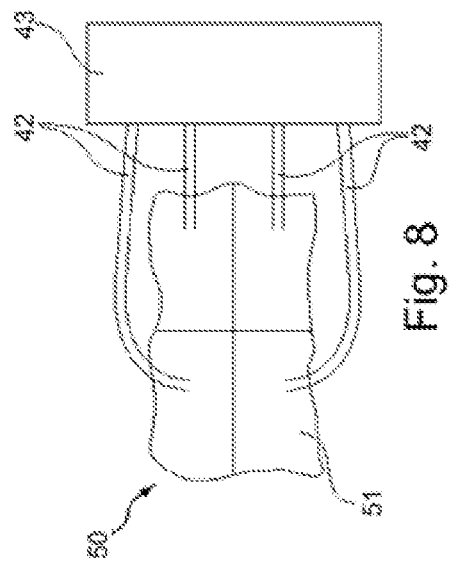

SENSOR FOR CONTACTLESS ELECTROCARDIOGRAPHIC MEASUREMENT

CROSS-REFERENCE TO RELATED APPLICATIONS

This application claims foreign priority benefits under 35 U.S.C. § 119(a)-(d) to DE 10 2013 216 682.6 filed Aug. 22, 2013, which is hereby incorporated by reference in its entirety.

TECHNICAL FIELD

The present invention relates to a sensor for a contactless electrocardiographic measurement on a person. Furthermore, the invention relates to a sensor array equipped with a plurality of sensors, and to a seat or couch in a vehicle, equipped with a sensor array.

BACKGROUND

Measuring the electric potential or the electric field strength on the skin of a person by means of electrocardiographic sensors forms the basis for many medical diagnostic methods. By way of example, this allows an electrocardiogram (EKG) to be recorded or the heart rate to be established from the measured electric potentials.

In conventional methods for measuring the electric potential on the skin, said electric potential is registered by electrodes which are in direct electric contact with the skin surface. Thus, an electrically conductive connection between the skin and the electrode is established. However, it is found often to be difficult to ensure a sufficiently good electric contact between the electrode and the skin, and hence the body of the person to be examined. Moreover, the use of such diagnostic methods is increasingly also envisaged in fields of application in which there is no direct access to the skin of the person to be examined, such as e.g. in vehicle applications for monitoring bodily functions and/or vital parameters of vehicle occupants on seats or couches.

Thus, for example, U.S. Pat. No. 7,684,854 B2 discloses a sensor for a contactless electrocardiographic measurement on a person. In this case, the person can be situated on a chair, in a bed or on a vehicle seat. The electrocardiogram can be recorded from the body of the person wearing clothes, without direct contact to the skin. The sensor comprises an electrically conductive, substantially flat electrode, which has a measurement area facing the person and a connection area facing away from the person and lying opposite to the measurement area, which connection area is electrically connected to a preamplifier. The electrode and the preamplifier of the sensor are surrounded by a shield.

A further contactless sensor for recording an electrocardiogram of a person is disclosed in EP 2 532 306 A1. The sensor comprises an electrically conductive electrode and a detection apparatus, which is electrically connected to the electrode and configured to amplify the signals recorded by the electrode. The sensor is provided to be arranged in a vehicle seat and to establish certain physiological parameters of a driver sitting in the vehicle seat.

DE 20 2012 001 096 U1 discloses capacitive sensors for registering vital parameters of a driver of a vehicle. To this end, the sensors are attached in, or on, the back of the seat of the vehicle. In particular, in accordance with one embodiment, it is proposed to arrange the sensors in, or on, the back of the seat in two rows separated from one another by a distance corresponding to the width of the spinal column of the driver. In each row, the sensors with an area of 16 to 36 cm$^2$ are arranged at equal distances of 1 to 5 cm from one another. In a further embodiment, two film sensors with a width of between 4 and 10 cm, separated from one another with a distance corresponding to the spinal column, are arranged over the whole height of the seat instead of the two sensor rows, separated from one another, with sensors distributed over the whole height of the seat at a distance of 1-5 cm.

Furthermore, DE 10 2008 049 112 A1 discloses a capacitive textile electrode for measuring bodily functions and/or vital parameters of persons for vehicle applications, for example in a seat or a couch, which electrode has a multi-layered design. The latter comprises two textile layers, which each have an electrically conductive electrode region, wherein a further textile layer is provided for establishing a distance between the two other textile layers.

In order to obtain a reliable and stable signal from the known sensors or sensor arrangements/arrays for a contactless electrocardiographic measurement on persons in vehicle applications, it is essential that the sensors are covered, at best completely, by the body or the body region to be examined of the person, and that a distance which is as small as possible is ensured between the sensors and the person to be examined. In general, those electrodes which have a large distance, e.g. to the back of the person to be examined, lead to a poor or even unusable signal.

Therefore, in principle, attempts can be made to place the sensors e.g. on a seat or couch area where a contact, which is as good as possible, is to be expected between the person situated in the seat or on the couch and the seat or the couch. However, in the case of relatively slim persons—due to their low weight—or in the case of persons which have an anatomical deformation such as e.g. lumbar hyperlordosis, it will be relatively difficult to ensure a sufficiently high contact pressure and a sufficiently large contact area between the measurement area of the electrode and the person to be examined. It follows that, particularly in the case of such persons, the probability of low quality measurement signals recorded by the electrode will increase.

SUMMARY

The present invention is based on the object of specifying a sensor, a sensor array and a seat or a couch for a contactless electrocardiographic measurement on persons, preferably in vehicle applications, by means of which reliable evaluations can be made of the bodily functions and/or vital parameters of the person, i.e. which are able to supply a reliable signal with high signal quality at all times.

Attention is drawn to the fact that the features listed individually in the claims can be combined with one another in any technically expedient manner and highlight further configurations of the invention. The description additionally characterizes and specifies the invention, in particular in conjunction with the figures.

According to an embodiment disclosed herein, a sensor for a contactless electrocardiographic measurement on a person, preferably in vehicle applications, comprises a two-dimensional (substantially flat) carrier for fastening the sensor on an object and at least one electrically conductive, two-dimensional electrode, which lies opposite the carrier and is connected to the latter. Within the scope of the present invention, "contactless" should be understood to mean that the electrode does not directly touch the skin of the person to be examined. By way of example, pieces of clothing can be arranged between the person to be examined and the electrode.

Furthermore, in the sensor disclosed herein, provision is made for a mechanism by means of which it is possible to change the distance between the electrode and the carrier. Therefore, with the aid of the disclosed sensor, it is possible in the case of the contactless electrocardiographic measurement on a person to bring the electrode facing the person closer to the person to be examined and thereby to increase the contact pressure and the contact area between the electrode and the person, as a result of which the quality of the measurement signal recorded by the electrode is increased and reliable evaluations can be made of the bodily functions and/or vital parameters of the person.

In accordance with one advantageous configuration disclosed herein, a bellows which can be filled with a gas and/or a fluid is interposed between the electrode and the carrier. By increasing the pressure in (inflating) the bellows, it is therefore possible in a simple manner to increase the distance between the electrode and the carrier and therefore it is possible to move the electrode of the sensor, fastened on an object, e.g. a vehicle seat or a couch, by means of the carrier, in the direction of the person to be examined. The fluid used to inflate the bellows can consist of a suitable gas, a liquid such as hydraulic and/or electrically conductive liquid, and any mixture of gas and liquid. Surrounding air is also suitable as gas.

A further advantageous configuration of a sensor disclosed herein provides for the bellows to have a plurality of independently inflatable chambers, as a result of which only the regions of the electrode corresponding to the respective chambers can be impinged upon by a higher or lower pressure in a targeted manner. Therefore, the sensor can be adapted even more precisely to the form of the body part, of the person to be examined, in contact with the electrode or said sensor can be modified even more precisely in its relative alignment with respect to the carrier.

In order to be able to control the application of pressure in a more targeted manner, provision, in accordance with a further advantageous configuration of the disclosed sensor, is made for a pressure sensor for registering the pressure present in the bellows and/or a distance sensor for registering the distance between the electrode and the carrier.

A further advantageous configuration of a sensor disclosed herein provides for the electrode to be formed from a flexible, electrically conductive electrode material. Therefore, the electrode is able to modify the form thereof dependent on the pressure present in the bellows and thus increase the contact pressure and the contact area to the person to be examined in an even simpler manner. Furthermore, the sensor can be adapted even more precisely to the form of the body part, of the person to be examined, in contact with the electrode.

A sensor array disclosed herein comprises at least two sensors of the above-described type. Within the meaning of the present invention, a sensor array should be understood to mean any type of arrangement of a plurality of these sensors. The particular advantage of such a sensor array should be seen in the fact that the mechanism can move only the electrodes of individual sensors from a multiplicity of sensors in a targeted manner so as to increase the contact pressure or the contact area between the corresponding sensor and the person to be examined (local increase in contact pressure or contact area).

In accordance with a disclosed embodiment, a seat or a couch in a vehicle comprises at least one sensor array in accordance with the above-described type, for a contactless electrocardiographic measurement on a person situated on the seat or the couch.

Further features and advantages of the invention emerge from the following description of exemplary embodiments of the invention, which are not to be construed as being restrictive and are explained in more detail below with reference to the drawing.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In the various figures, the same parts have always been provided with the same reference signs, and so these are generally also only described once.

Figure 1:
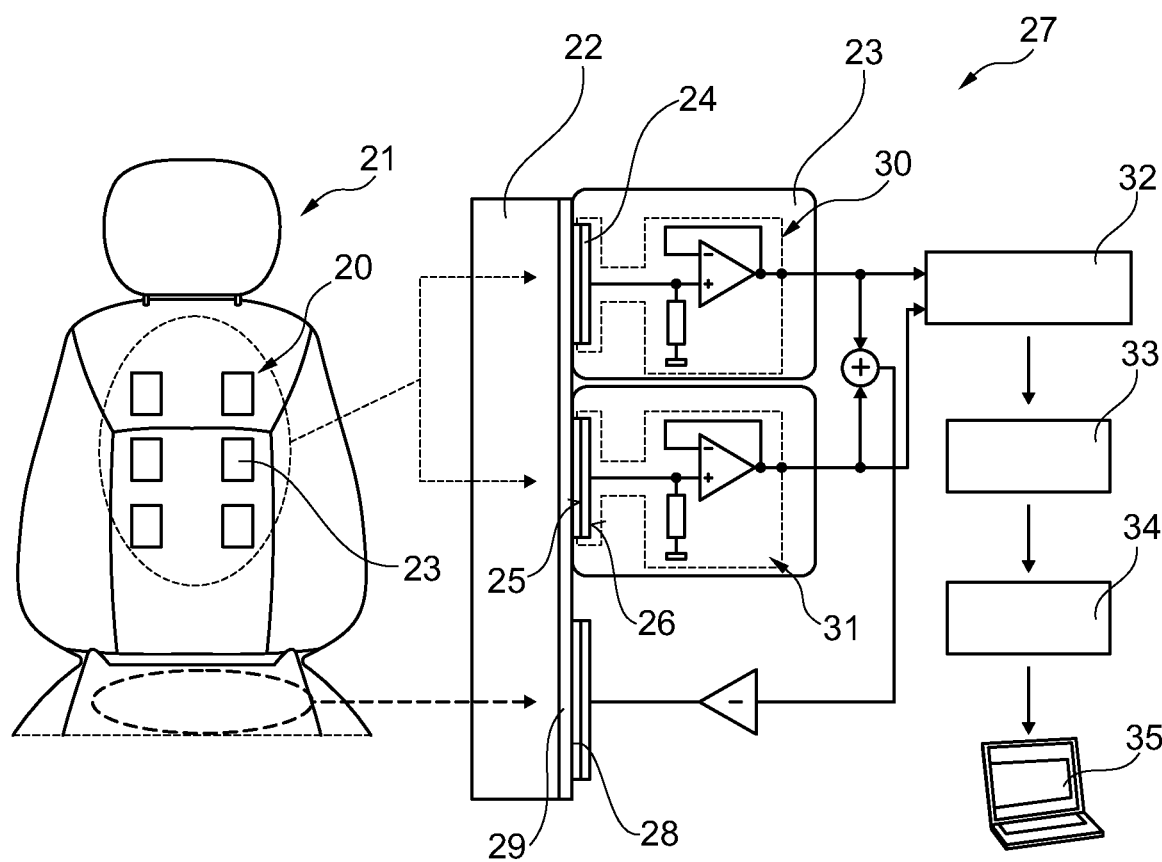
FIG. 1 schematically shows a sensor array and a seat for a vehicle in accordance with the prior art, FIG. 2 schematically shows a cross-sectional view of a sensor in accordance with a first embodiment in a first operating position, FIG. 3 schematically shows a cross-sectional view of the sensor from FIG. 2 in a second operating position, FIG. 4 schematically shows a cross-sectional view of a sensor in accordance with a further embodiment, FIG. 5 schematically shows a cross-sectional view of a sensor in accordance with an even further embodiment, FIG. 6 schematically shows a top view of a bellows in accordance with a first embodiment, FIG. 7 schematically shows a side view of a bellows in accordance with a further embodiment, FIG. 8 schematically shows a top view of a bellows in accordance with a further embodiment, and FIG. 9 schematically shows a top view of a bellows in accordance with a further embodiment.

FIG. 1 schematically depicts a sensor array 20 and a seat 21 for a vehicle, for a contactless electrocardiographic measurement on a person 22, according to the prior art. It is possible to identify that the sensor array consists of a matrix-like arrangement of six sensors 23 arranged in a back of a vehicle seat in a 3×2 matrix, which sensors each have an electrically conductive, two-dimensional (substantially flat) electrode 24. Furthermore, a further electrode is arranged in the seating area of the vehicle seat 21, by means of which further electrode a reference potential of the circuit is applied.

Each electrode 24 comprises a measurement area 25 facing the person 22 or their body, and a connection area 26 facing away from the person and lying opposite to the measurement area 25, for a connection to a measurement apparatus 27. As depicted in FIG. 1, the measurement area 25 of the individual electrodes 24 does not directly contact the skin of the person 22 to be examined. Rather, insulation 28 has been applied onto the measurement area 25 of each electrode 24 in FIG. 1. Moreover, the clothes 29 worn by the person are additionally also situated between the body of the person 22 to be examined and the insulation 28.

The measurement apparatus 27 depicted in FIG. 1 comprises one preamplifier 31, surrounded by a shield 30, per sensor 23. Furthermore, an instrument amplifier 32 amplifies the measurement signal recorded by the electrodes 24 of the sensors 23; this is followed by a filter and amplification unit 33 and an A/D transducer 34. The digital measurement signal output by the A/D transducer 34 can subsequently be processed further in a suitable manner by means of e.g. a digital computer 35.

FIG. 2 schematically depicts a cross-sectional view of a sensor 36, in accordance with a first embodiment, according to the invention in a first operating position, whereas FIG. 3 depicts the sensor 36 in a second operating position. The sensor 36 comprises a two-dimensional (substantially flat) carrier 37 for fastening the sensor 36 on an object, e.g. a back of a vehicle seat, in particular in a position on the seat back that corresponds to a lordotic (inwardly curved or arched) region of a seat occupant's back, but also in other regions with reduced contact force, and furthermore an electrically conductive, two-dimensional (substantially flat) electrode 24, which lies opposite the carrier 37 and is connected to the latter. In the exemplary embodiment of the sensor 36 shown in FIGS. 2 and 3, the electrode 24 is connected to the carrier 37 by means of elastic support elements 38, preferably made of foam, which are arranged on the edge of the electrode 24.

FIGS. 2 and 3 show that a mechanism 39, by means of which it is possible to change the distance between the electrode 24 and the carrier 37, is provided at the sensor 36. In particular, in the shown exemplary embodiment, the mechanism 39 is embodied in the form of a bellows 40 which can be inflated with a gas, e.g. air, and/or a fluid and which is interposed between the electrode 24 and the carrier 37. In the operating position depicted in FIG. 2, the bellows 40 is substantially empty (deflated), whereas the bellows 40 in the operating position depicted in FIG. 3 is inflated with the gas, preferably air. FIGS. 2 and 3 show that the distance between the electrode 24 and the carrier 37 can be modified with the aid of the bellows 40 in accordance with the gas volume contained in the bellows 40 and hence the electrode 24 can be moved relative to the carrier 37. By way of example, if the sensor 36 is attached to a back of a vehicle seat by means of the carrier 37, this allows the contact pressure and the contact area between a person sitting on the vehicle seat and the electrode 24 to be increased such that the electrode 24 of a measurement apparatus (not depicted in FIGS. 2 and 3), which is electrically connected to the electrode 24, is able to reliably supply a measurement signal with a high signal quality.

Figure 4:
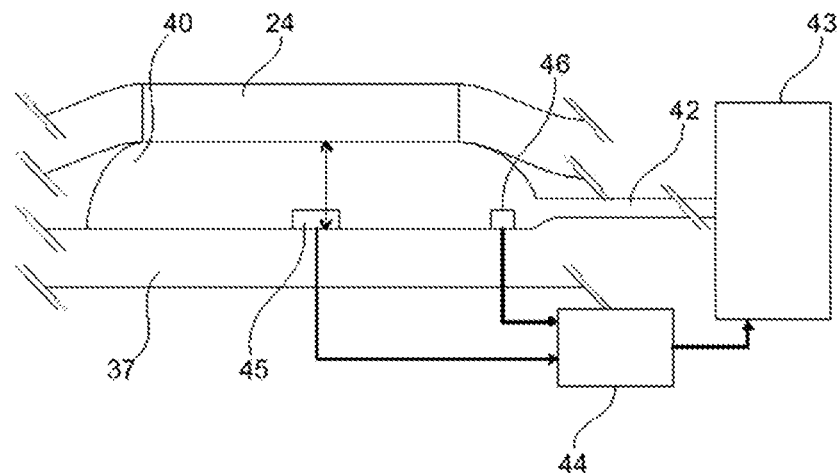

FIG. 4 depicts a cross-sectional view of a sensor 41 according to the invention in accordance with a further embodiment. The sensor 41, like the sensor 36 depicted in FIGS. 2 and 3, comprises a two-dimensional carrier 37 for fastening the sensor 41 on an object, for example a back of a vehicle seat, in particular in a lordotic region of the back, but also in other regions with a reduced contact force, and furthermore an electrically conductive, two-dimensional electrode 24, which lies opposite the carrier 37 and is connected to the latter. Furthermore, a bellows 40 which can be inflated with a gas, e.g. air, and is inserted between the electrode 24 and the carrier 37 is part of the sensor 41 shown in FIG. 3. The bellows 40 can be inflated and deflated by a pump 43 connected to the bellows 40 by a tube 42. The pump 43 can be controlled by an electronic control module 44 in the embodiment depicted in FIG. 4.

In the sensor 41 shown in FIG. 4, a distance sensor 45 and a pressure sensor 46 are provided in the bellows 40 for targeted control of the flow of gas between the pump 43 and the bellows 40. The sensors 45 and 46 are each electrically connected to the control module 44. The distance sensor 45 serves for registering the distance between the electrode 24 and the carrier 37. The pressure sensor 46 serves for registering the gas pressure present in the bellows 40. Both sensors 45 and 46 supply corresponding sensor signals to the control module 44, with the aid of which sensor signals the control module 44 controls the gas volume to be supplied by the pump 43.

Figure 5:
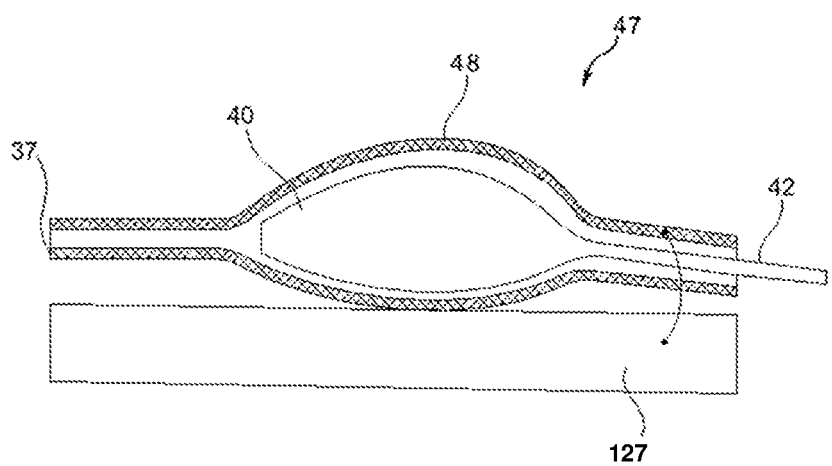

FIG. 5 depicts a cross-sectional view of a sensor 47 according to the invention, in accordance with an even further embodiment. Distinguishing from the sensors 36 and 41 according to the previously described embodiments, the sensor 47 comprises an electrode 48 which is formed from a flexible, electrically conductive electrode material. Hence, the electrode 48 in this case deforms in accordance with the inflation state of the bellows 40 and thus increases the contact pressure and/or the contact area between the electrode 48 and a person (not shown in FIG. 5) to be examined by means of the sensor 47. In this manner, the sensor 47 fits even more closely to the body part of the person to be examined.

Furthermore, FIG. 5 depicts a measurement apparatus 127, which is electrically connected to the electrode 48 and which prepares the measurement signals recorded by the electrode 48 in a similar manner to the measurement apparatus 27 depicted in FIG. 1.

FIGS. 6 to 9 depict four different embodiments of bellows according to the invention. In FIG. 6, the bellows 40 is depicted in a top view in a simplest form, embodied like a bladder. FIG. 7 depicts bellows embodied as concertina-type bellows 49 in a side view. The two tubes 42 depicted in FIG. 7 are to be understood as alternative embodiments. FIG. 8 depicts multi-chamber bellows 50 with four chambers 51, which can be inflated independently from one another, in a top view. FIG. 9 depicts a further type of multi-chamber bellows 52 with four chambers 53, which can be inflated independently from one another, in a top view. FIGS. 8 and 9 show that the multi-chamber bellows 50 and 52 differ in terms of their different arrangement of the chambers 51 and 53.

The sensor according to the invention, the sensor array and the seat or the couch were explained in more detail on the basis of a plurality of exemplary embodiments depicted in the figures. However, the sensor, the sensor array and the seat or the couch are not restricted to the embodiments described herein, but rather also comprise further embodiments with a similar action.

In a preferred embodiment, the sensor according to the invention, the sensor array and the seat or the couch are used in a vehicle, in particular a motor vehicle, for a contactless electrocardiographic measurement on a person.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A contactless electrocardiographic sensor, comprising:
a carrier for mounting the sensor to an object;

an electrocardiographic measurement electrode supported by the carrier for movement relative thereto, wherein the electrode comprises a two-dimensional, electrically conductive electrode;

a bellows disposed between the carrier and the electrode, the bellows selectively inflatable and deflatable to selectively move the electrode toward and away, respectively, from a person without contacting the person to obtain a contactless electrocardiographic measurement;

a pressure sensor registering a pressure in the bellows; and an electronic control module receiving signals from the pressure sensor and controlling inflation of the bellows in response thereto.

2. Apparatus for electrocardiographic measurement of a person seated on a seat having a seat back, comprising:

a carrier adapted for mounting to the seat back;

an electrically conductive electrocardiographic measurement electrode connected with the carrier by an elastic element;

a bellows disposed between the carrier and the electrode, inflation of the bellows deflecting the elastic element to move the electrode away from the carrier toward the person without the electrode contacting the person;

a pressure sensor registering a pressure in the bellows; and an electronic control module receiving signals from the pressure sensor and controlling inflation of the bellows in response thereto.

3. A seat comprising:

a bellows;

a pump in fluid communication with the bellows;

an electrically conductive electrocardiographic measurement electrode disposed on the bellows;

an electronic control module actuating the pump to inflate the bellows urging the electrode toward a person seated on the seat without contacting the person with the electrode to provide a contactless electrocardiographic measurement; and a pressure sensor registering a pressure in the bellows and sending signals to the control module for use in controlling the pump.

* * * * *